(12) United States Patent
Tal (10) Patent No.: US 11,541,206 B2
(45) Date of Patent: Jan. 3, 2023

(54) REMOVABLE CATHETER CAP AND APPLICATIONS THEREOF

(71) Applicant: Pristine Access Technologies LTD, Tel-Aviv (IL)

(72) Inventor: Michael Gabriel Tal, Savyon (IL)

(73) Assignee: Pristine Access Technologies LTD., Tel Aviv (IL)

( * ) Notice: Subject to any disclaimer, the term of this patent is extended or adjusted under 35 U.S.C. 154(b) by 1133 days.

(21) Appl. No.: 16/079,170

(22) PCT Filed: Feb. 28, 2017

(86) PCT No.: PCT/IB2017/051183
§ 371 (c)(1),
(2) Date: Aug. 23, 2018

(87) PCT Pub. No.: WO2017/149465
PCT Pub. Date: Sep. 8, 2017

(65) Prior Publication Data
US 2019/0054272 A1 Feb. 21, 2019

Related U.S. Application Data

(60) Provisional application No. 62/301,013, filed on Feb. 29, 2016.

(51) Int. Cl.
*A61M 25/00* (2006.01)
*A61M 25/01* (2006.01)
(Continued)

(52) U.S. Cl.
CPC ...... *A61M 25/0069* (2013.01); *A61M 25/008* (2013.01); *A61M 25/0074* (2013.01);
(Continued)

(58) Field of Classification Search
CPC .......... A61M 25/0069; A61M 25/0074; A61M 2025/0079; A61M 2025/0063
See application file for complete search history.

(56) References Cited

U.S. PATENT DOCUMENTS 5,156,592 A    10/1992   Martin et al.
5,647,857 A *   7/1997   Anderson ............... A61F 2/958
                                                                                       604/160

(Continued)

FOREIGN PATENT DOCUMENTS

CN        101918066 B    7/2013
EP         1610853 A1    1/2006
(Continued)

OTHER PUBLICATIONS

International Search Report and Written Opinion dated Jun. 5, 2016 in International Patent Application No. PCT/IB2017/051183.

*Primary Examiner* — Bhisma Mehta
*Assistant Examiner* — John J Crawford
(74) *Attorney, Agent, or Firm* — Rutan & Tucker LLP (57) ABSTRACT

Removable catheter cap, and applications thereof, for delivering medical tubes in bodily passages. Removable catheter cap covers flexible medical tube (e.g., catheter) distal tip during delivery in a body lumen. Catheter cap includes: cap body removably connectable to, for capping, catheter distal tip, and transformable into a predefined constituent part freely passable through catheter lumen; and cap releasing member extending through catheter proximal end when catheter cap is connected to the catheter, and manipulatable for transforming cap body into constituent part or/and for withdrawing constituent part from catheter distal tip through catheter lumen. Exemplary applications are: provision of a catheter assembly including a catheter and the removable catheter cap connected thereto; a medical kit including one or more catheters and one or more correspondingly config- (Continued)

ured removable catheter caps; and a method for delivering a catheter in a blood vessel of a subject, for example, via an over-the-wire technique.

19 Claims, 7 Drawing Sheets

(51) Int. Cl.
*A61B 17/00* (2006.01)
*A61B 17/34* (2006.01)
*A61B 90/00* (2016.01)

(52) U.S. Cl.
CPC ... *A61M 25/01* (2013.01); *A61B 2017/00473* (2013.01); *A61B 2017/3456* (2013.01); *A61B 2090/08021* (2016.02); *A61M 2025/0031* (2013.01)

(56) References Cited

U.S. PATENT DOCUMENTS

| | | | |
|---|---|---|---|
| 5,752,937 A * | 5/1998 | Otten | A61M 25/0668 604/161 |
| 5,800,414 A | 9/1998 | Cazal | |
| 5,947,953 A | 9/1999 | Ash et al. | |
| 6,001,079 A | 12/1999 | Pourchez | |
| 6,110,146 A * | 8/2000 | Berthiaume | A61M 25/09041 604/103 |
| 6,482,169 B1 | 11/2002 | Kuhle | |
| 6,513,527 B1 | 2/2003 | Abdel-Aziz | |
| 7,108,674 B2 | 9/2006 | Quinn | |
| 7,182,746 B2 | 2/2007 | Haarala et al. | |
| 7,776,005 B2 | 8/2010 | Haggstrom et al. | |
| 8,066,660 B2 | 11/2011 | Gregersen et al. | |
| 8,092,415 B2 | 1/2012 | Moehle et al. | |
| 9,539,411 B2 * | 1/2017 | Cully | A61M 25/0045 |
| 10,213,578 B2 * | 2/2019 | Fukuoka | A61M 25/0069 |
| 11,026,669 B2 * | 6/2021 | Castelli | A61B 17/34 |
| 2002/0052641 A1 | 5/2002 | Monroe et al. | |
| 2002/0062129 A1 | 5/2002 | Mikus et al. | |
| 2003/0153898 A1 | 8/2003 | Schon et al. | |
| 2004/0092863 A1 | 5/2004 | Raulerson et al. | |
| 2004/0167463 A1 | 8/2004 | Zawacki et al. | |
| 2005/0054989 A1 | 3/2005 | McGuckin et al. | |
| 2005/0277862 A1 | 12/2005 | Anand | |
| 2006/0025781 A1 | 2/2006 | Young et al. | |
| 2006/0149350 A1 | 7/2006 | Patel et al. | |
| 2007/0208276 A1 | 9/2007 | Volk et al. | |
| 2007/0225661 A1 | 9/2007 | Ash et al. | |
| 2008/0142005 A1 * | 6/2008 | Schnell | A61M 16/0472 128/207.29 |
| 2009/0137944 A1 | 5/2009 | Haarala et al. | |
| 2009/0204052 A1 | 8/2009 | Nimkar et al. | |
| 2009/0204079 A1 | 8/2009 | Nimkar et al. | |
| 2009/0209940 A1 | 8/2009 | Nimkar et al. | |
| 2011/0011525 A1 | 1/2011 | Sanscoucy | |
| 2012/0130392 A1 | 5/2012 | Levy et al. | |
| 2012/0143123 A1 | 6/2012 | Agnew | |
| 2012/0179102 A1 * | 7/2012 | Blanchard | A61B 17/3415 604/164.1 |
| 2012/0209201 A1 * | 8/2012 | Bellisario | A61B 17/3415 604/164.01 |
| 2013/0324964 A1 | 12/2013 | Florescu | |
| 2014/0261407 A1 | 9/2014 | Roberts et al. | |

FOREIGN PATENT DOCUMENTS

| | | |
|---|---|---|
| EP | 1792637 A2 | 6/2007 |
| EP | 2277579 A1 | 1/2011 |
| EP | 2446915 B1 | 1/2018 |
| WO | 91/015255 A1 | 10/1991 |
| WO | 97/009086 A1 | 3/1997 |
| WO | 03/045464 A2 | 6/2003 |

* cited by examiner

REMOVABLE CATHETER CAP AND APPLICATIONS THEREOF

RELATED APPLICATIONS

This application claims the benefit of priority under 35 USC 119(e) of U.S. Provisional Patent Application No. 62/301,013, filed 29 Feb. 2016, entitled "Atraumatic Cap for Medical Tubes and Catheters", the contents of which are incorporated herein by reference in their entirety.

FIELD OF THE INVENTION

The present invention, in some embodiments thereof, relates to devices and methods for delivering a medical tube in a bodily passage, and more particularly, but not exclusively, to a removable catheter cap for covering the distal tip of a flexible medical tube, such as a catheter (e.g., a single or multiple lumen or tip catheter or a blunt-tip catheter), during delivery of the medical tube in a body lumen. Exemplary applications of the invention are: provision of a catheter assembly including a catheter and the removable catheter cap connected thereto; a medical kit including one or more catheters and one or more correspondingly configured removable catheter caps; and a method for delivering a catheter in a blood vessel of a subject.

BACKGROUND OF THE INVENTION

In common practice, various medical tubes, such as catheters, are introduced into body lumens for performing a treatment, which can be local (e.g., dilatation of a narrowed portion of a vessel wall) or systemic (e.g., drug delivery via the vascular system), temporary or acute (e.g., deployment of a stent), or chronic (e.g., using a chronic hemodialysis catheter).

Catheters are commonly delivered to a target location in a blood vessel using the 'Seldinger technique', which most basically includes placing a guidewire from an entry point to the blood vessel and across the target location, passing an introducer sheath over the guidewire, optionally withdrawing the guidewire, and then delivering the catheter, via the introducer sheath, until reaching the target location. The introducer sheath serves as a closed track or channel in which the catheter and other instrumentation can be delivered.

When performing temporary or short term catheterization procedures, it is customary that the introducer sheath is removed from the body only after removing the catheter and any other relevant instrumentation. However, when the catheter is intended for long-term placement or implantation, the catheter can be introduced via a 'peelable' vascular sheath. This type of introducer sheath can be removed from the blood vessel while the implanted catheter remains in-place, by first splitting, tearing, or/and peeling portions of the sheath around the catheter, for example, along perforated tear lines or other weakened spots. Such technique is known practice for placing different types of catheters and other medical tubes, for example: tunneled dialysis catheters, peripherally inserted central catheter (PICC), port for central venous catheter, or delivery or extraction of pacemaker leads.

Use of a peelable sheath may be accompanied by potential failures, mostly due to anatomy or conditions of the host blood vessel. Vein laceration is an injury to vein walls that may occur during delivery of a peelable sheath, for example, due to buckling of the guidewire and inadvertent advancement of the dilator portion of the sheath through the vein (e.g., the superior vena cava), possibly, when the sheath is advanced through the vein over a relatively lax guidewire.

Structural characteristics of some catheters may also be found disadvantageous in current uses thereof. For example, catheters having a distal tip being fully blunt, substantially soft, or having an inadequate guidewire opening, cannot be used effectively, or at all, in deliveries over a guidewire or/and without a sheath. Blunt and soft catheter distal tips may also increase likelihood of delivery failures associated with peelable sheath applications. Other catheters, such as ones used for transcatheter aortic valve replacement (TAVR) surgeries, have relatively sharp or pointed tips, or/and optionally relatively rigid, which may cause injury to surrounding tissue (e.g., puncturing of heart tissue). Catheters may have only side holes, for example the Foley catheter for draining the urine bladder, and it may be advantageous to have their distal tip be blunt shaped, with a forward opening instead or in addition to the side holes. Some other medical tubes designs may limit intubation techniques, for example drainage or chest tubes which are currently inserted while grasping their distal tip with a 'Kelly' clamp, thereby causing discomfort to the patient.

In view of such shortcomings, as well as other limitations, in the field and art of the invention, there is need for developing and practicing new or/and improved devices, and applications thereof, for delivering medical tubes (such as catheters) in bodily passages.

SUMMARY OF THE INVENTION

The present invention, in some embodiments thereof, relates to devices and methods for delivering a medical tube in a bodily passage, and more particularly, but not exclusively, to a removable catheter cap for covering the distal tip of a flexible medical tube, such as a catheter (e.g., a single or multiple lumen or tip catheter or a blunt-tip catheter), during delivery of the medical tube in a body lumen, for example, via an over-the-wire insertion technique. Exemplary applications of the invention are: provision of a catheter assembly including a catheter and the removable catheter cap connected thereto; a medical kit including one or more catheters and one or more correspondingly configured removable catheter caps; and a method for delivering a catheter in a blood vessel of a subject.

According to an aspect of some embodiments of the present invention, there is provided a removable catheter cap, comprising: a cap body configured for being removably connectable to distal tip of a catheter, so as to facilitate capping of the catheter distal tip, and is sized and shaped for blocking passage of the cap body through a lumen of the catheter extending from the catheter distal tip to proximal end of the catheter, the cap body is transformable into at least one predefined constituent part that is sized and shaped to freely pass through the catheter lumen; and a cap releasing member configured to extend through the catheter proximal end when the removable catheter cap is connected to the catheter, and is selectively manipulatable for facilitating transformation of the cap body into the at least one constituent part or/and for facilitating withdrawal of the at least one constituent part from the catheter distal tip through the catheter lumen.

According to some embodiments of the invention, the cap body is configured to provide space between the catheter distal tip and surrounding tissue during delivery of the catheter within a blood vessel. According to some embodiments of the invention, the cap body has a shape or form that is tapered, ogival, or/and streamlined for facilitating traversability of the catheter in a blood vessel. According to some embodiments of the invention, the cap body is configured to reinforce a distal portion of the catheter when the removable catheter cap is connected to the catheter.

According to some embodiments of the invention, the removable catheter cap is configured as an atraumatic cap, wherein the cap body is more flexible, smoother, or/and softer than the catheter distal tip.

According to some embodiments of the invention, the cap releasing member is, or is operatively connected to, an end portion of the predefined constituent part that emerges from the cap body, and is extendable across the catheter lumen when the removable catheter cap is connected to the catheter. According to some embodiments of the invention, the cap releasing member is selectively manipulatable for facilitating disconnection and release of the cap body from connection to the catheter distal tip.

According to some embodiments of the invention, the cap body includes a guidewire opening sized for passing a guidewire therethrough, so as to facilitate passage of the catheter, when connected to the removable catheter cap, over the guidewire in a blood vessel. According to some embodiments of the invention, the cap body comprises a cap vertex and a cap base, wherein the cap body is configured with a cap cavity that spans between the cap vertex and the cap base, and the cap body is configured for housing the catheter distal tip. According to some embodiments of the invention, the cap body includes splittable or/and peelable lines or portions that are configured to facilitate the transformation of the cap body into the at least one predefined constituent part by separating the cap body along the splittable or/and peelable lines or portions. According to some embodiments of the invention, the cap body includes separable windings of the at least one predefined constituent part. According to some embodiments of the invention, the separable windings are interbonded, intertwined, or/and woven. According to some embodiments of the invention, the separable windings are configured to separate into the at least one predefined constituent part when the cap body is pulled against the catheter distal tip. According to some embodiments of the invention, the separable windings are configured to separate when the cap body is pulled against the catheter distal tip only above a predetermined pulling force.

According to some embodiments of the invention, the at least one predefined constituent part has an unwound free end configured as, or operatively connected to, an elongated pulling member, the pulling member is configured for transferring a pulling force to the cap body. According to some embodiments of the invention, the cap releasing member includes, extends from, or is connected to, the elongated pulling member.

According to some embodiments of the invention, the cap body includes, or is releasably connected to, a first extension sized and configured for insertion into the catheter lumen. According to some embodiments of the invention, the first extension, when extending into the catheter lumen, is configured to reinforce a distal portion of the catheter.

According to some embodiments of the invention, the catheter is a split-tip catheter comprising at least a first tip and a second tip, wherein the cap body is configured for releasably adjoining distal end-portions of the at least first and second tips.

According to an aspect of some embodiments of the present invention, there is provided a removable catheter cap, comprising: a cap body configured for being removably connectable to distal tip of a catheter, so as to facilitate capping of the catheter distal tip, and is sized and shaped for blocking passage of the cap body through a lumen of the catheter extending from the catheter distal tip to proximal end of the catheter, and the cap body includes interbonded, intertwined, or/and woven separable windings of at least one predefined constituent part that is sized and shaped to freely pass through the catheter lumen; wherein the separable windings are configured to separate into the at least one predefined constituent part when the cap body is pulled against the catheter distal tip.

According to some embodiments of the invention, the at least one predefined constituent part has an unwound free end portion configured as, or operatively connected to, an elongated pulling member, the pulling member is configured for transferring a pulling force to the cap body.

According to some embodiments of the invention, the removable catheter cap further comprises a cap releasing member that is configured to extend through the catheter proximal end, when the removable catheter cap is connected to the catheter, and is selectively manipulatable for facilitating transformation of the cap body into the at least one constituent part or/and for facilitating withdrawal of the at least one constituent part from the catheter distal tip through the catheter lumen. According to some embodiments of the invention, the cap releasing member is, or is operatively connected to, an end portion of the predefined constituent part that emerges from the cap body, and is extendable across the catheter lumen when the removable catheter cap is connected to the catheter.

According to an aspect of some embodiments of the present invention, there is provided a catheter assembly, comprising: a catheter having a catheter lumen extending from a distal tip to a proximal end of the catheter; and a removable catheter cap releasably connected to the catheter and comprising: a cap body configured for being removably connectable to the catheter distal tip, so as to facilitate capping of the catheter distal tip, and sized and shaped for blocking passage of the cap body through the catheter lumen, the cap body is transformable into at least one predefined constituent part that is sized and shaped to freely pass through the catheter lumen; and a cap releasing member configured to extend through the catheter proximal end when the removable catheter cap is connected to the catheter, and is selectively manipulatable for facilitating transformation of the cap body into the at least one constituent part or/and for facilitating withdrawal of the at least one constituent part from the catheter distal tip through the catheter lumen.

According to an aspect of some embodiments of the present invention, there is provided a catheter assembly, comprising: a catheter having a catheter lumen extending from a distal tip to a proximal end of the catheter; and a removable catheter cap releasably connected to the catheter and comprising a cap body configured for being removably connectable to the catheter distal tip, so as to facilitate capping of the catheter distal tip, and sized and shaped for blocking passage of the cap body through the catheter lumen, the cap body includes interbonded, intertwined, or/and woven separable windings of at least one predefined constituent part that is sized and shaped to freely pass through the catheter lumen; wherein the separable windings are configured to separate into the at least one predefined constituent part when the cap body is pulled against the catheter distal tip.

According to an aspect of some embodiments of the present invention, there is provided a medical kit, comprising: at least one catheter; and at least one removable catheter cap, each one of the at least one removable catheter cap is comprised of a cap body configured for being removably connectable to distal tip of a corresponding one of the at least one catheter, so as to facilitate capping of the catheter distal tip, and is sized and shaped for blocking passage of the cap body through a lumen of the corresponding catheter extending from the catheter distal tip to proximal end of the corresponding catheter, and the cap body includes interbonded, intertwined, or/and woven separable windings of at least one predefined constituent part that is sized and shaped to freely pass through the catheter lumen; wherein the separable windings are configured to separate into the at least one predefined constituent part when the cap body is pulled against the catheter distal tip.

According to some embodiments of the invention, the at least one predefined constituent part has an unwound free end portion configured as, or operatively connected to, an elongated pulling member, the pulling member is configured for transferring a pulling force to the cap body.

According to some embodiments of the invention, the removable catheter cap further comprises a cap releasing member that is configured to extend through the catheter proximal end, when the removable catheter cap is connected to the corresponding catheter, and is selectively manipulatable for facilitating transformation of the cap body into the at least one constituent part or/and for facilitating withdrawal of the at least one constituent part from the catheter distal tip through the catheter lumen. According to some embodiments of the invention, the cap releasing member is, or is operatively connected to, an end portion of the predefined constituent part that emerges from the cap body, and is extendable across the catheter lumen when the removable catheter cap is connected to the corresponding catheter.

According to an aspect of some embodiments of the present invention, there is provided a method for delivering a catheter in a blood vessel, the method comprising: inserting a guidewire in the blood vessel and across a target location; capping distal tip of the catheter with a removable catheter cap comprising a cap body having a guidewire opening sized for passing the guidewire therethrough; passing the guidewire through the guidewire opening, into and across a lumen of the catheter, to a proximal end of the catheter; pushing the catheter with the removable catheter cap thereon in the blood vessel and over the guidewire until reaching the target location; and transforming the cap body into at least one predefined constituent part that is sized and shaped to pass freely through the catheter lumen.

According to some embodiments of the invention, the removable catheter cap includes a cap releasing member, and wherein the transforming includes manipulating the cap releasing member from the catheter proximal end. According to some embodiments of the invention, the cap releasing member includes, or is operatively connected to, an elongated pulling member extendable from the removable catheter cap through the catheter distal tip and to the catheter proximal end, wherein the transforming includes pulling the elongated pulling member.

According to some embodiments of the invention, the method further comprises removing the at least one constituent part from the blood vessel via the catheter lumen.

According to some embodiments of the invention, the cap body is sized and shaped for blocking passage of the cap body through the catheter lumen, and includes separable windings of the at least one predefined constituent, the method further comprising: separating the separable windings by pulling the cap body against the catheter distal tip via an unwound free end portion of the at least one predefined constituent part.

According to some embodiments of the invention, the catheter is a split-tip catheter comprising at least a first tip and a second tip, wherein the capping includes holding the first and second tips adjoined to each other with the cap body, and wherein the transforming facilitates releasing the adjoined first and second tips.

All technical or/and scientific words, terms, or/and phrases, used herein have the same or similar meaning as commonly understood by one of ordinary skill in the art to which the invention pertains, unless otherwise specifically defined or stated herein. Exemplary embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

BRIEF DESCRIPTION OF THE DRAWINGS

Some embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how some embodiments of the present invention may be practiced.

In the drawings.

DESCRIPTION OF SPECIFIC EMBODIMENTS OF THE INVENTION

The present invention, in some embodiments thereof, relates to devices and methods for delivering a medical tube in a bodily passage, and more particularly, but not exclusively, to a removable catheter cap for covering the distal tip of a flexible medical tube, such as a catheter (e.g., a single or multiple lumen or tip catheter or a blunt-tip catheter), during delivery of the medical tube in a body lumen, for example, via an over-the-wire insertion technique. Exemplary applications of the invention are: provision of a catheter assembly including a catheter and the removable catheter cap connected thereto; a medical kit including one or more catheters and one or more correspondingly configured removable catheter caps; and a method for delivering a catheter in a blood vessel of a subject.

An aspect of some embodiments of the present invention is provision of a removable catheter cap, including a cap body configured for being removably connectable to distal tip of a catheter, so as to facilitate capping of the catheter distal tip. In exemplary embodiments, the cap body is sized and shaped for blocking passage of the cap body through a lumen of the catheter extending from the catheter distal tip to proximal end of the catheter. In exemplary embodiments, the cap body is transformable into at least one predefined constituent part that is sized and shaped to freely pass through the catheter lumen. In exemplary embodiments, the removable catheter cap further includes a cap releasing member configured to extend through the catheter proximal end when the removable catheter cap is connected to the catheter, and is selectively manipulatable for facilitating transformation of the cap body into the at least one constituent part or/and for facilitating withdrawal of the at least one constituent part from the catheter distal tip through the catheter lumen.

An aspect of some embodiments of the present invention is provision of a removable catheter cap, including a cap body having interbonded, intertwined, or/and woven separable windings of at least one predefined constituent part that is sized and shaped to freely pass through the lumen of a catheter, wherein the separable windings are configured to separate into the at least one predefined constituent part when the cap body is pulled against the catheter distal tip.

An aspect of some embodiments of the present invention is provision of a catheter assembly, including a catheter, and a removable catheter cap releasably connected to the catheter. In exemplary embodiments, the catheter has a lumen extending from the catheter distal tip to the catheter proximal end. In exemplary embodiments, the removable catheter cap includes a cap body and a cap releasing member. In exemplary embodiments, the cap body is configured for being removably connectable to the catheter distal tip, so as to facilitate capping of the catheter distal tip, and sized and shaped for blocking passage of the cap body through the catheter lumen. In exemplary embodiments, the cap body is transformable into at least one predefined constituent part that is sized and shaped to freely pass through the catheter lumen. In exemplary embodiments, the cap releasing member is configured to extend through the catheter proximal end when the removable catheter cap is connected to the catheter, and is selectively manipulatable for facilitating transformation of the cap body into the at least one constituent part or/and for facilitating withdrawal of the at least one constituent part from the catheter distal tip through the catheter lumen.

An aspect of some embodiments of the present invention is provision of a medical kit, including at least one catheter, and at least one removable catheter cap. In exemplary embodiments, each one of the at least one removable catheter cap includes a cap body configured for being removably connectable to the distal tip of a corresponding one of the at least one catheter. In exemplary embodiments, the cap body facilitates capping of the catheter distal tip, and is sized and shaped for blocking passage of the cap body through a lumen of the corresponding catheter extending from the catheter distal tip to proximal end of the corresponding catheter.

An aspect of some embodiments of the present invention is provision of a method for delivering a catheter in a blood vessel, the method including: inserting a guidewire in the blood vessel and across a target location; capping the distal tip of the catheter with a removable catheter cap that includes a cap body having a guidewire opening sized for passing the guidewire therethrough; passing the guidewire through the guidewire opening, into and across a lumen of the catheter, to a proximal end of the catheter; pushing the catheter with the removable catheter cap thereon in the blood vessel and over the guidewire until reaching the target location; and transforming the cap body into at least one predefined constituent part that is sized and shaped to pass freely through the catheter lumen. In exemplary embodiments, the removable catheter cap includes a cap releasing member, and the transforming includes manipulating the cap releasing member from the catheter proximal end.

In exemplary embodiments, the cap releasing member includes, or is operatively connected to, an elongated pulling member extendable from the removable catheter cap through the catheter distal tip and to the catheter proximal end, the transforming includes pulling the elongated pulling member. The pulling member is optionally configured for transferring a pulling force to the cap body. For example, the cap releasing member may be in a form of a handheld element that is connected or joined to the elongated pulling member being in a form of a pull-wire. Alternatively, the cap releasing member may be a first portion (e.g., more proximal portion) and the elongated pulling member may be a second portion (e.g., a more distal portion) of a same element (e.g., a pull-wire). Optionally, additionally or alternatively, the cap releasing member is, or is operatively connected to, an end portion of the predefined constituent part that emerges from the cap body. Optionally, additionally or alternatively, the at least one predefined constituent part has an unwound (or non-wound) free end configured as, or operatively connected to, the elongated pulling member. In some embodiments, the cap releasing member or/and the elongated pulling member is a portion of the predefined constituent part, or, more particularly, of the unwound (or non-wound) free end thereof.

In exemplary embodiments, the method further includes removing the at least one constituent part from the blood vessel via the catheter lumen. In exemplary embodiments, the cap body is sized and shaped for blocking passage of the cap body through the catheter lumen, and includes separable windings of the at least one predefined constituent, and the method further includes separating the separable windings by pulling the cap body against the catheter distal tip via an unwound free end portion of the at least one predefined constituent part. In exemplary embodiments, the catheter is a split-tip catheter including at least a first tip and a second tip, and the capping includes holding the first and second tips adjoined to each other with the cap body, and the transforming facilitates releasing the adjoined first and second tips.

For purposes of better understanding exemplary embodiments of the present invention, in the following illustrative description thereof, reference is made to the figures (FIGS. 1 through 7). Throughout the following description and accompanying drawings, same reference numbers refer to same components, elements, or features. It is to be understood that the invention is not necessarily limited in its application to any particular sequential ordering of method steps or procedures, or to particular details of construction or/and arrangement of apparatus (device) components, set forth in the following illustrative description. The invention is capable of other embodiments or of being practiced or carried out in various ways, including a surgical tool or catheter or hollow tube of any sort.

Figure 1A:
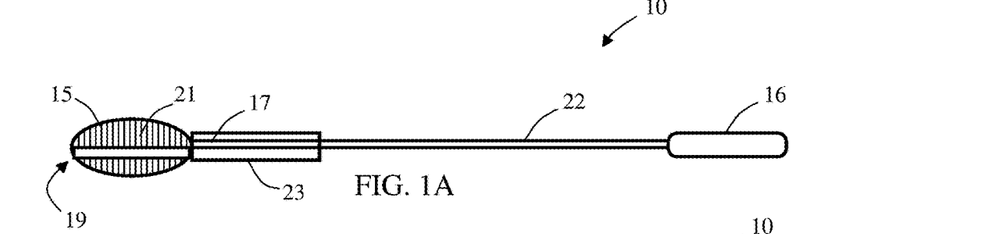
FIG. 1A is a schematic sectional orthogonal view of an exemplary removable catheter cap, in accordance with some embodiments of the invention.
Figure 1B:
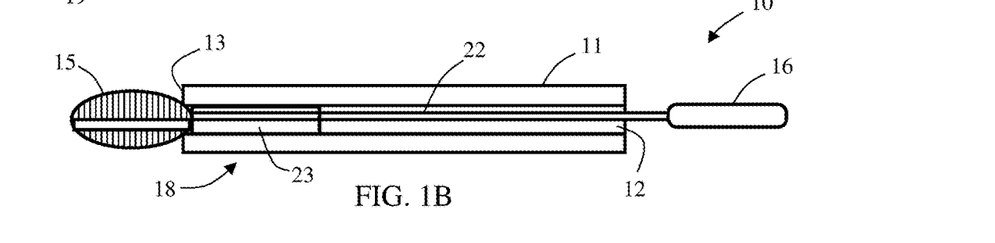
FIGS. 1B-1E are schematic sectional orthogonal views of the exemplary removable catheter cap (of FIG. 1A), connected to an exemplary medical tube (such as a catheter), in possible exemplary deployments thereof, in accordance with some embodiments of the invention.
Figure 1C:
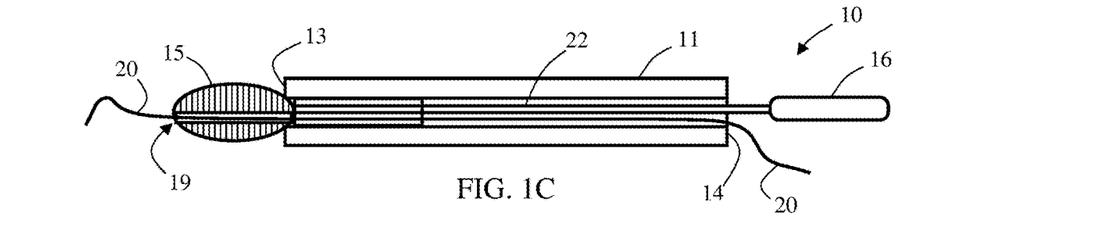
Figure 1D:
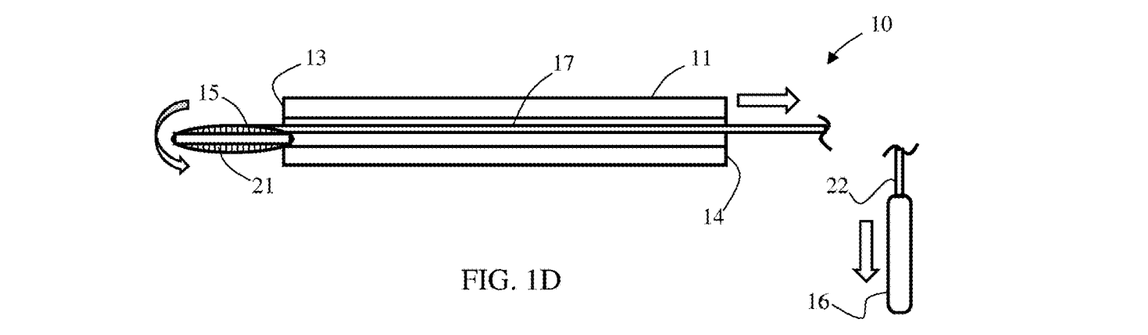
Figure 1E:
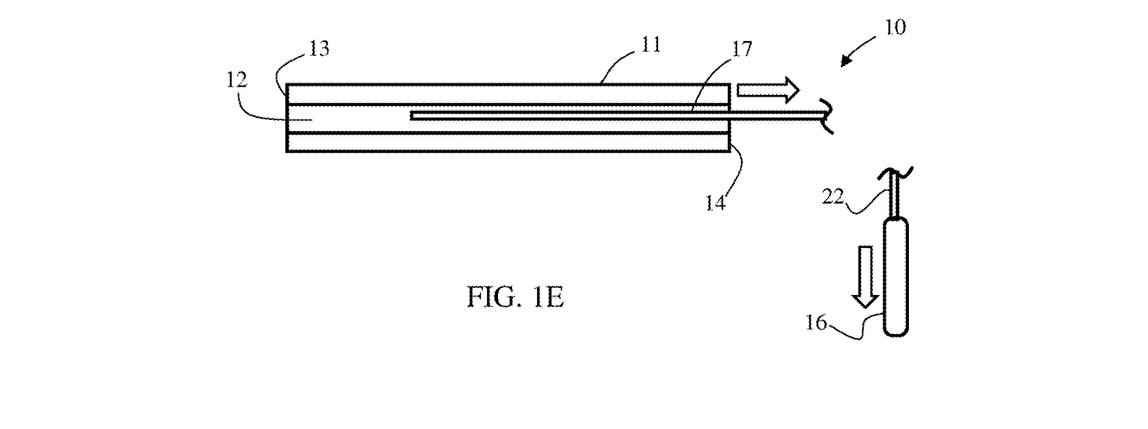

FIG. 1A is a schematic sectional orthogonal view of an exemplary removable catheter cap 10. FIGS. 1B-1E are schematic sectional orthogonal views of the exemplary removable catheter cap 10, connected to an exemplary medical tube, such as a catheter 11, in possible exemplary deployments thereof. Removable catheter cap 10 is configured to connect to catheter 11, in order to improve safety, efficacy, comfort or/and ease in delivering catheter 11 in a blood vessel.

Catheter 11 has a catheter lumen 12 extending from a distal tip 13 thereof to a proximal end 14 thereof. In some embodiments, catheter distal tip 13 is blunt so that capping it with the catheter cap 10 provides a front geometry being advantageous for improving traversability in a blood vessel. The removable catheter cap 10 may also serve and be configured as an atraumatic cap, by which it improves protection of surrounding tissue (e.g., blood vessel wall) during delivery.

Removable catheter cap 10 includes a cap body 15 and a cap releasing member 16. Cap body 15 is configured to cap catheter distal tip 13 when the removable catheter cap 10 is connected to catheter 11. As such, cap body 15 provides space between catheter distal tip 13 and surrounding tissue (blood vessel wall) during delivery of catheter 11 within a blood vessel.

Upon delivery to a chosen position, cap 10 (e.g., cap body 15) is disconnected from catheter 11 and removed from the blood vessel, in order to allow use of catheter 11 at the target location. For having it removed, cap body 15 is first reshaped or/and sized to allow its (or parts thereof) passing through the catheter (e.g., through a lumen in the catheter). Such reshaping and resizing may involve changing its structure, for example, by transforming of one or more components or portions thereof. The term 'transforming', as used herein, refers to any of the following possibilities or any combination thereof: separating, breaking, cracking, cutting, splitting, disjoining, detaching, dividing, unraveling, unwrapping, dismantling, disconnecting, tearing and disassembling, either into a single element or to a number of pieces, fragments or parts. Optionally, cap body 15 includes separable windings, which may be interbonded, intertwined or/and woven, and the transforming may include separation by force of this windings, into forming an at least one constituent part.

Cap body 15 is sized, shaped or/and configured to block passing thereof through catheter lumen 12. Cap body 15 has a shape or form that is tapered (e.g., ogival), at least in front (distal) portion thereof, and streamlined, for facilitating traversability of catheter 11 in the blood vessel. Cap body 15 includes a guidewire opening 19 sized for passing a guidewire 20 therethrough, so as to facilitate passage of catheter 11, when connected to the removable catheter cap 10, over guidewire 20 in a blood vessel.

Cap body 15 is transformable into at least one predefined constituent part 17 that is sized, shaped or/and configured to freely pass through catheter lumen 12. Cap body 15 may include splittable or/and peelable lines or portions 21, configured to facilitate cap body separability into the at least one predefined constituent part 17 along the splittable or/and peelable lines or portions 21. Optionally, additionally or alternatively, cap body 15 is fabricated from at least one bonded, intertwined or/and woven elongated pulling member 22, that forms the at least one predefined constituent part 17 when separated from the bonded or/and woven fabrication of cap body 15.

Cap releasing member 16 is configured to extend through catheter proximal end 14 when the removable catheter cap 10 is connected to catheter 11. Cap releasing member 16 emerges from cap body 15 and is extendable across catheter lumen 12, when the removable catheter cap 10 is connected to catheter 11. Cap releasing member 16 is selectively manipulatable to separate cap body 15 into at least one constituent part 17 and to withdraw (e.g., by pulling) the constituent part 17 from catheter distal tip 13 through catheter lumen 12. As such, cap releasing member 16 is selectively manipulatable for releasing cap body 15 from connection to catheter distal tip 13.

In some embodiments, cap body 15 is configured to separate into at least one predefined constituent part 17 when pulled against catheter distal tip 13, optionally only above a predetermined pulling force, using elongated pulling member 22. Accordingly, cap releasing member 16 extends from elongated pulling member 22 (but may include it or be connected thereto).

In some embodiments, cap body 15 reinforces a distal portion 18 of catheter 11 when the removable catheter cap 10 is connected thereto. Cap body 15 is releasably connected to an at least one extension 23 that is sized and configured for insertion into catheter lumen 12, optionally snugly fits thereinside. Extension 23 may be one of the predefined constituent parts 17. When extending into catheter lumen 12, extension 23 is configured to reinforce catheter distal portion 18.

Reference is made to FIGS. 2A-2D which are schematic side cut views representing possible scenarios of implementing exemplary embodiments of a method for atraumatic deployment of a medical tube in a form of a catheter 100 in a blood vessel BV by protecting or/and holding a distal (front) end portion 101 of the catheter 100 with an atraumatic removable catheter cap 102, for example by covering a distal blunt tip 103 of catheter 100.

Atraumatic removable catheter cap 102 includes a cap body 104 which encloses a cap cavity 105 between a cap vertex 106 and a cap base 107. Cap body 104 is sized and configured for housing distal end portion 101 of catheter 100 with the blunt tip 103, in cap cavity 105. Cap vertex 106 includes a guidewire opening 109 sized for passing a guidewire GW therethrough into a first lumen 110 opened at blunt tip 103, via cap cavity 105, for allowing progress of the catheter with the atraumatic removable catheter cap thereon into the body and into a blood vessel BV over guidewire GW (e.g. by using an "over-the-wire" technique).

Figure 2A:
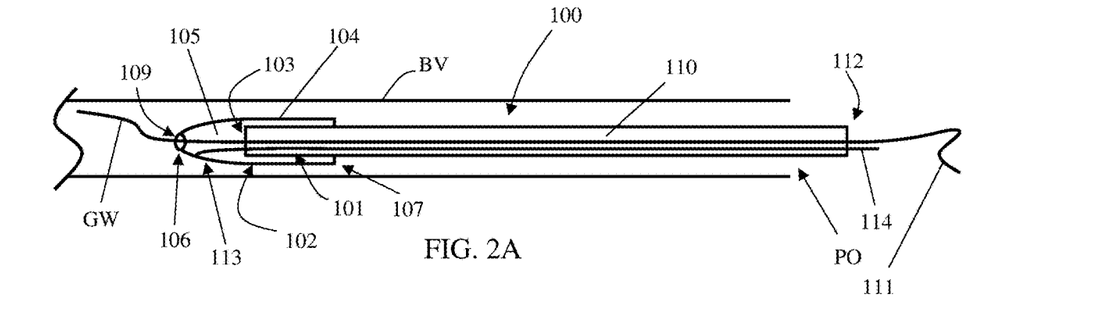
FIGS. 2A-2D are schematic sectional orthogonal views representing possible scenarios of implementing exemplary embodiments of a method for atraumatic deployment of a catheter in a body lumen, in accordance with some embodiments of the invention.

Catheter 100 is shown in FIG. 2A readily provided in blood vessel BV capped with atraumatic removable catheter cap 102, over a guidewire GW. In some embodiments, deploying of catheter 100 may include:

inserting guidewire GW into the body and into the blood vessel BV from a preformed opening PO to across a target location TL therein;

capping distal end-portion 101 of catheter 100 with atraumatic removable catheter cap 102;

passing a proximal end 111 of guidewire GW through guidewire opening 109 into first lumen 110 of the catheter 100, via cap cavity 105, until guidewire proximal end 111 protrudes out a proximal end 112 of catheter 100; and pushing the catheter 100 with the atraumatic removable catheter cap 102 thereon in the blood vessel BV over the guidewire GW until reaching the target location.

Figure 2B:
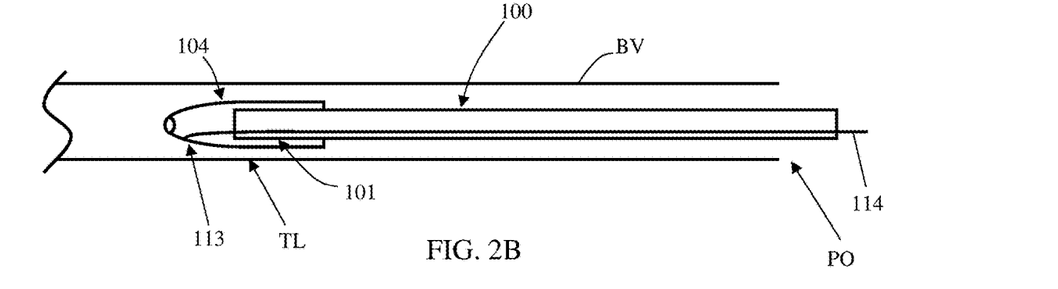

After deploying catheter 100 in blood vessel BV, the guidewire GW may be removed (as shown in FIG. 2B).

Atraumatic removable catheter cap 102 further includes a cap releasing member 113 which is sized and configured for passing along or/and through the catheter 100 and for operating release of cap body 104 from blunt tip 103 via proximal end 112 of the catheter 100. In some embodiments, cap body 104 is transformable (e.g., dismantlable into one or more pieces) and configured for selective separation into at least one predefined constituent part that is sized, shaped or/and configured to freely pass through catheter lumen 110, by activation of cap release member 113. Optionally, cap body 104 includes splittable or/and peelable lines or portions, or/and it may be fabricated from at least one bonded or/and woven elongated member. A maximal sized piece of these one or more pieces may be sized or/and compressible to a compressed size for allowing passage via a lumen of the catheter, such as first lumen 110. In some embodiments, the cap releasing member 113 includes an elongated pulling member that is optionally in a form of a pull-wire 114.

Figure 2C:
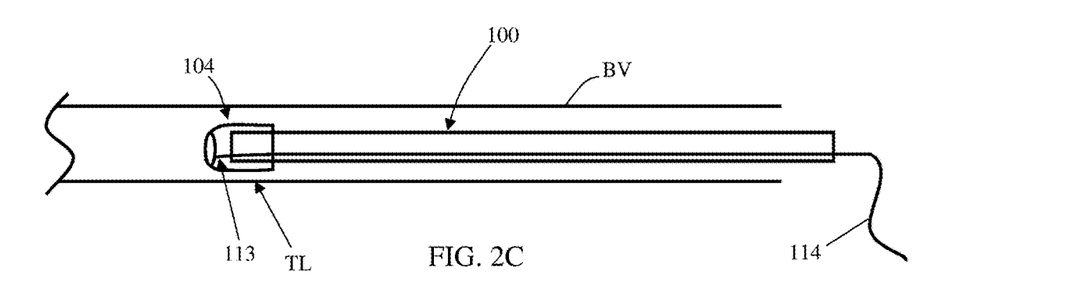
Figure 2D:
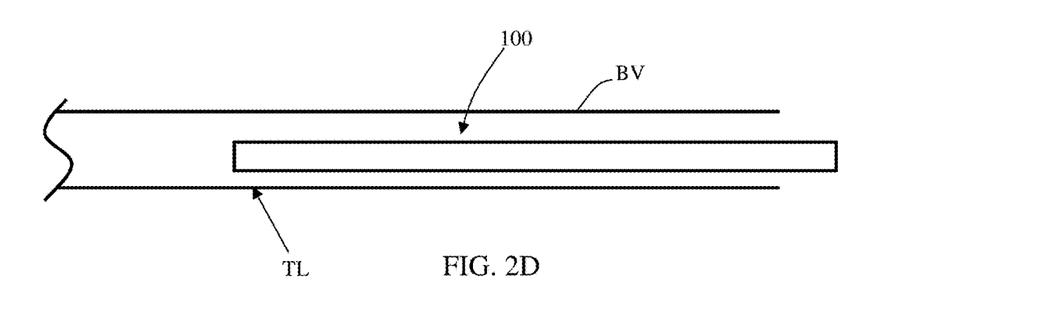

In some embodiments, exemplary steps for implementing deployment of catheter 100 in blood vessel BV may further include dismantling cap body 104. Dismantling may include activating cap releasing member 113 via proximal end 112 of the catheter, optionally by pulling pull-wire 114 (in a proximal direction). FIG. 2C shows catheter 100 during dismantling of cap body 104, in which the cap body is in reduced size. FIG. 2D shows catheter 100 after complete dismantling of cap body 104 and removal thereof from catheter 100 and blood vessel BV.

FIGS. 3A-3G are schematic side cut views representing possible scenarios of implementing exemplary embodiments of a method for deploying a split-tip catheter 200 in a blood vessel BV by protecting or/and holding a distal (front) end portion 201 of the catheter 200 with an atraumatic removable catheter cap 202, for example by covering a distal blunt tip (or tips) 203 of catheter 200.

Atraumatic removable catheter cap 202 includes a thin-walled cap body 204 which encloses a cap cavity 205 between a cap vertex 206 and a cap base 207. Cap body 204 is sized and configured for housing distal end portion 201 of catheter 200 with the blunt tip 203, in cap cavity 205. Cap vertex 206 includes a guidewire opening 209 sized for passing a guidewire GW therethrough into a first lumen 210 opened at blunt tip 203, via cap cavity 205, for allowing progress of the catheter with the atraumatic removable catheter cap thereon in blood vessel BV over guidewire GW (e.g. by using an "over-the-wire" technique).

Figure 3A:
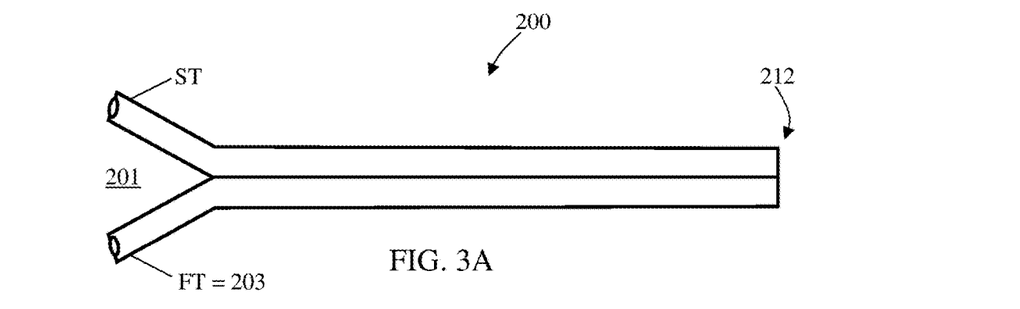
FIGS. 3A-3G are schematic sectional orthogonal views representing possible scenarios of implementing exemplary embodiments of a method for deploying a dual-tip catheter in a blood vessel, in accordance with some embodiments of the invention.
Figure 3B:
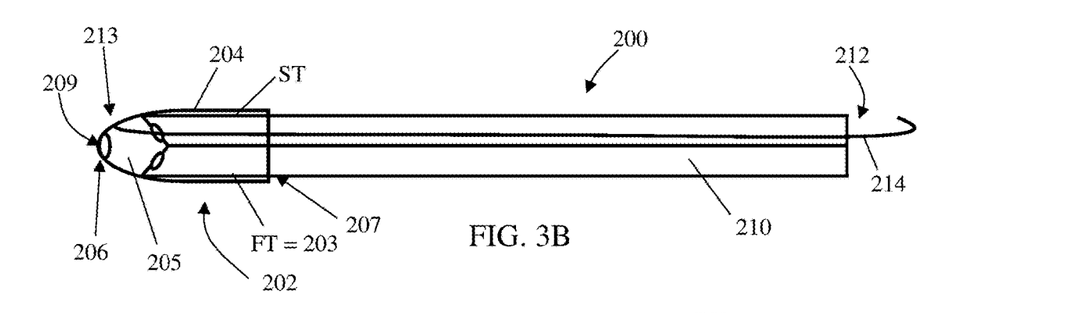
Figure 3C:
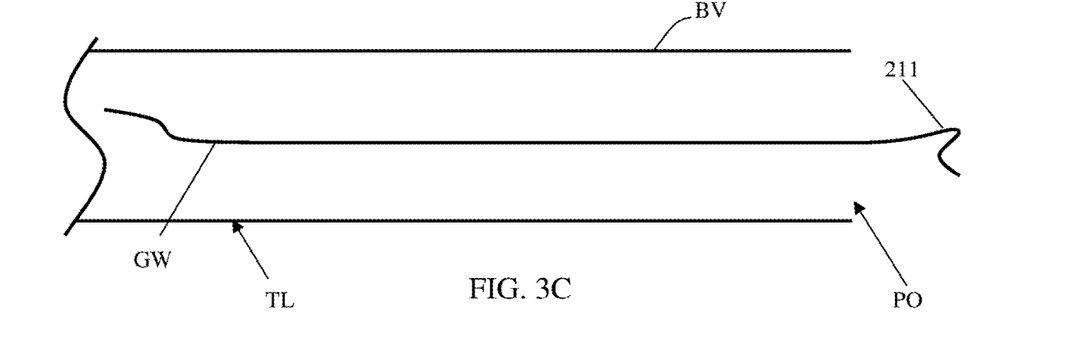
Figure 3D:
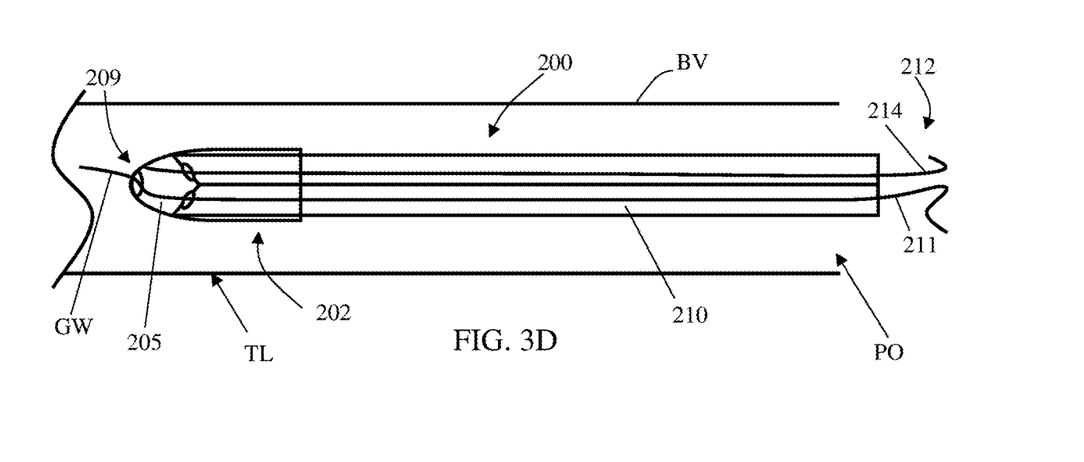

Catheter 200, shown uncapped in FIG. 3A, includes at least a first tip FT and a second tip ST, including blunt tip 203. Cap body 204 is configured for releasably adjoining distal end-portions of first FT and second ST tips of the split-tip catheter, and the cap base 207 is sized to span at least around these distal end-portions when adjoined. In some embodiments, deploying of catheter 200 may include:

adjoining first FT and second ST tips and capping distal end-portion 201 of catheter 200 with atraumatic removable catheter cap 202 including capping of the adjoined first FT and second ST (FIG. 3B);

inserting guidewire GW into the blood vessel BV from a preformed opening in the skin PO to across a target location TL therein (FIG. 3C);

passing a proximal end 211 of guidewire GW through guidewire opening 209 into first lumen 210 of the catheter 200, via cap cavity 205, until guidewire proximal end 211 protrudes out a proximal end 212 of catheter 200, and then pushing the catheter 200 with the atraumatic removable catheter cap 202 thereon in the blood vessel BV over guidewire GW until reaching the target location TL (FIG. 3D).

Figure 3E:
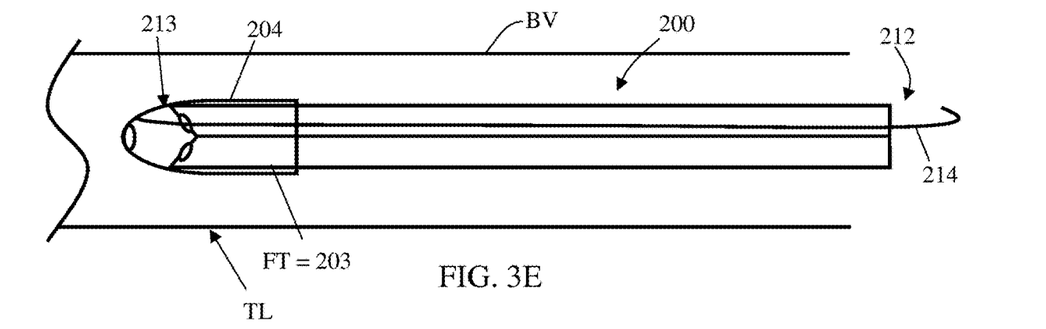

After deploying catheter 200 in blood vessel BV, the guidewire GW may be removed (as shown in FIG. 3E).

Atraumatic removable catheter cap 202 further includes a cap releasing member 213 which is sized and configured for passing along or/and through the catheter 200 and for operating release of cap body 204 from blunt tip 203 via proximal end 212 of the catheter 200. In some embodiments, cap body 204 is transformable (e.g., dismantlable into one or more pieces) and configured for selective separation into at least one predefined constituent part that is sized, shaped or/and configured to freely pass through a lumen of the catheter, such as first lumen 210, by activation of cap release member 213. Optionally, cap body 204 includes splittable or/and peelable lines or portions, or/and it may be fabricated from at least one bonded or/and woven elongated member. A maximal sized piece of these one or more pieces may be sized or/and compressible to a compressed size for allowing passage via a lumen of the catheter, such as first lumen 210. In some embodiments, the cap releasing member 213 includes an elongated pulling member that is optionally in a form of a pull-wire 214.

Figure 3F:
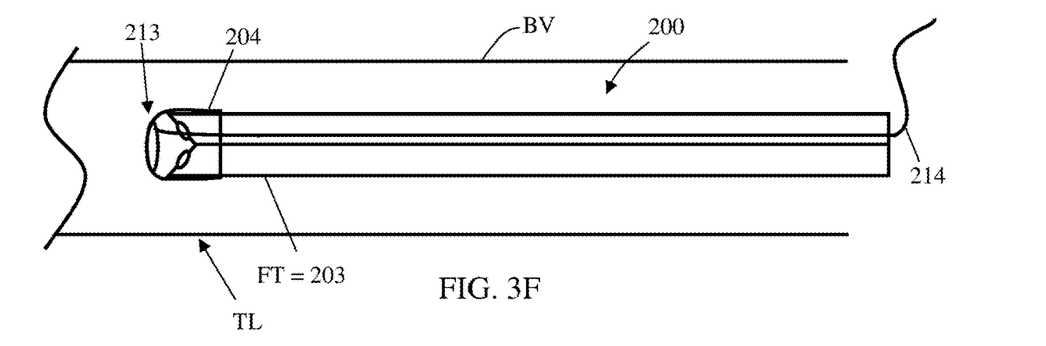
Figure 3G:
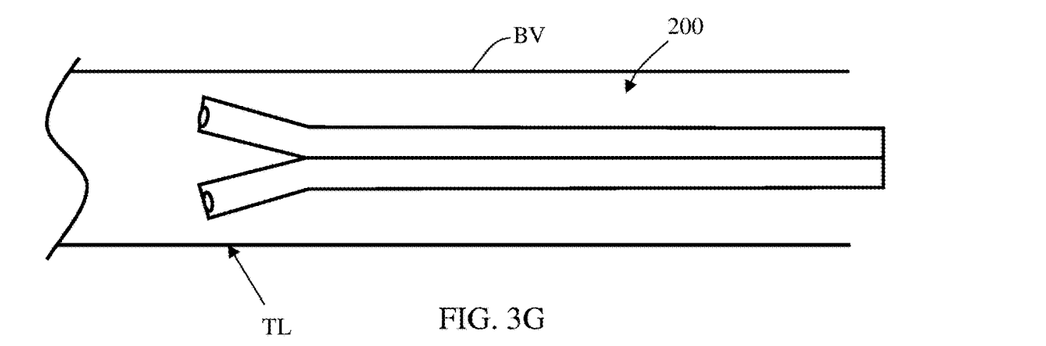

In some embodiments, exemplary steps for implementing deployment of catheter 200 in blood vessel BV may further include dismantling cap body 204. Dismantling may include activating cap releasing member 213 via proximal end 212 of the catheter, optionally by pulling pull-wire 214 (in a proximal direction). FIG. 3F shows catheter 200 during dismantling of cap body 204, in which the cap body is in reduced size. FIG. 3G shows catheter 200 after complete dismantling of cap body 204 and removal thereof from catheter 200 and blood vessel BV. Dismantling of cap body 204 may include or/and result with separation of the adjoined distal tips end-portions of the dual-tip catheter 200.

Figure 4:
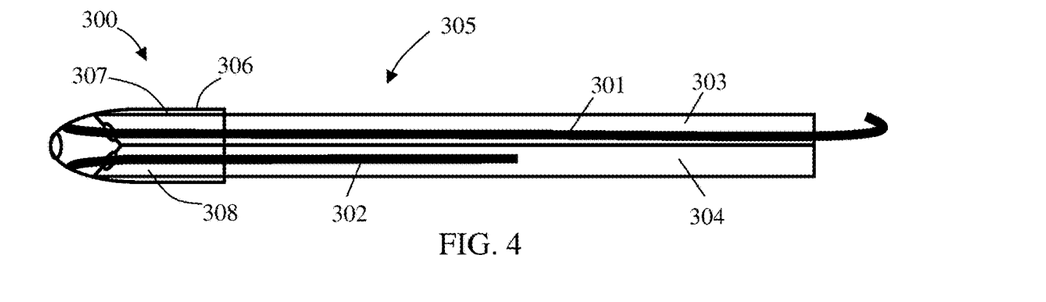
FIG. 4 is a schematic sectional orthogonal view of an exemplary removable catheter cap having two extensions provided in lumens of an exemplary double lumen catheter, in accordance with some embodiments of the invention.

FIG. 4 is a schematic cut view of an exemplary atraumatic removable catheter cap 300 having two extensions (a first extension 301 and a second extension 302) provided in lumens (a first lumen 303 and a second lumen 304) of an exemplary split-tip catheter 305. Atraumatic removable catheter cap 303 has cap body 306 which includes the first extension 301 and second extension 302. First extension 301 is sized and configured for insertion into first lumen 303 opened at a first distal (e.g., blunt) tip 307 of catheter 305, thereby reinforcing blunt tip 307 to withstand shaping of first lumen 303 by external forces acting on blunt tip. Cap body 306 also includes the second extension 302 sized and configured for insertion into the second lumen 304 opened at a second distal tip 308 of the split-tip catheter 305, thereby reinforcing second tip 308 to withstand shaping of second lumen 304 by external forces acting on the second tip 308. Any of the mentioned external forces may include at least one of bending forces, twisting forces, axially compressing forces, flattening forces and kinking forces.

Figures 5A, 5B, 6A:
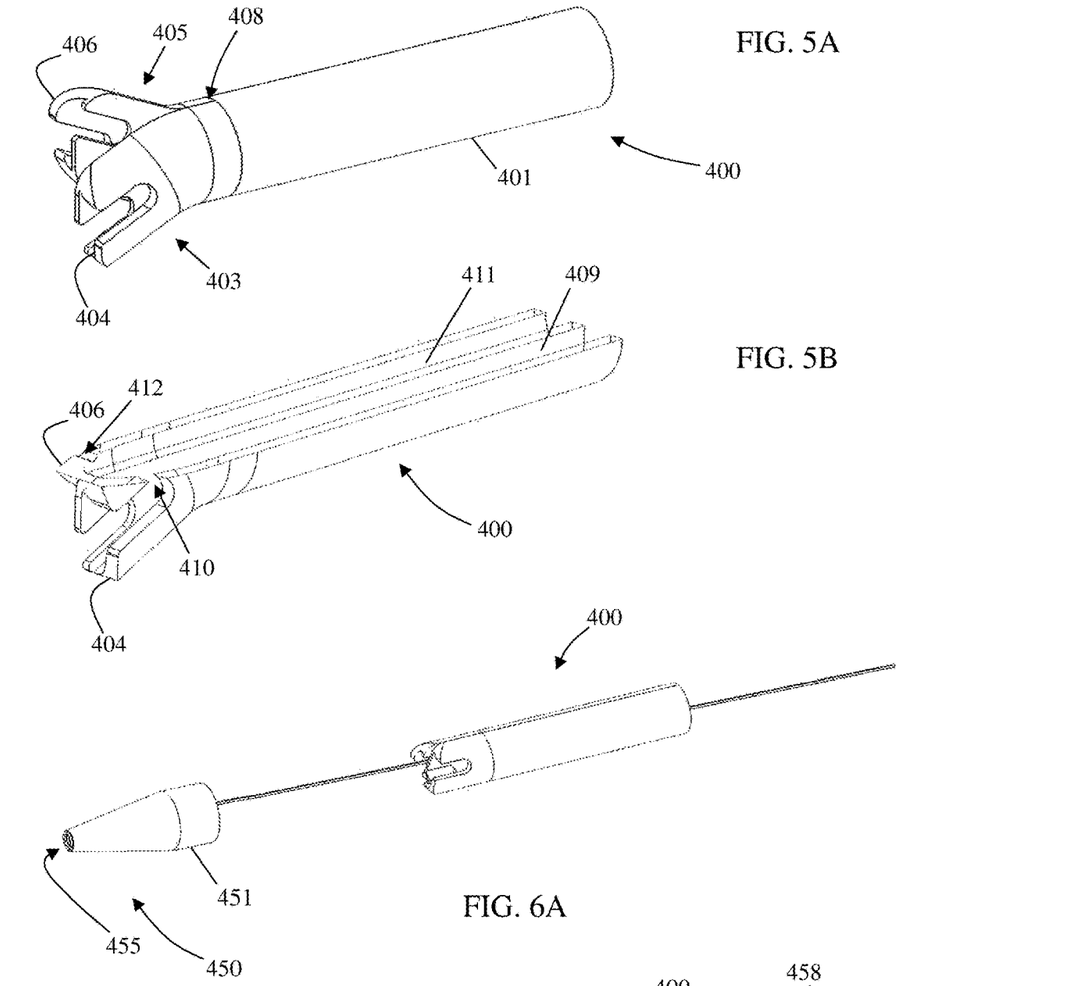
FIGS. 5A-5B are isometric views (full and sectional) of an exemplary dual-tip catheter prior to covering with an exemplary removable catheter cap, in accordance with some embodiments of the invention.
FIGS. 6A-6C are isometric views representing possible scenarios of implementing exemplary embodiments of a method for deploying the catheter of FIG. 5 with an exemplary removable catheter cap, in accordance with some embodiments of the invention.

FIGS. 5A-5B are isometric views (full and cut, respectively) of an exemplary split-tip catheter 400 prior to covering with atraumatic removable catheter cap. In some embodiments, catheter 400 is in a form of a hemodialysis catheter, optionally with a corrugated distal end. Catheter 400 includes an elongated body 401 (shown only with a front segment thereof), a first distal end region 403 terminating in a first tip 404, and a second distal end region 405 terminating in a second tip 406. The first 403 and second 405 distal end regions are separated with each other adjacent a junction 408. First distal end region 403 encloses a first lumen 409 opened to a first tip opening 410 provided at the first tip 404, and second distal end region 405 encloses a second lumen 411 opened to a second tip opening 412 provided at the second tip 406. First lumen 409 and second lumen 411 are independent one to the other for facilitating simultaneous flow in opposite directions, as required for effecting blood circulation.

Catheter 400 is shown at a fully deployed form in which the tips openings 410 and 412 are oriented to opposite directions one with each other. As such, first distal end region 403 and second distal end region 405 are optionally rotationally symmetric one with the other relative to a longitudinal axis of the catheter. According to some embodiments of the invention, elongated body 401 is elastically shapeable from a confined form, whereby the first 403 and second 405 end regions are forced to approximate each other within restricting boundaries, to the fully deployed form, whereby the first 403 and 405 second end regions are unconfined, such as with an atraumatic removable catheter cap, as will be further described below. Upon removal of any aligning or/and covering means, first distal end region 403 and second distal end region 405 may voluntarily slide against each other, such as in a scissor-like movement, up to the fully deployed form.

Figure 6B:
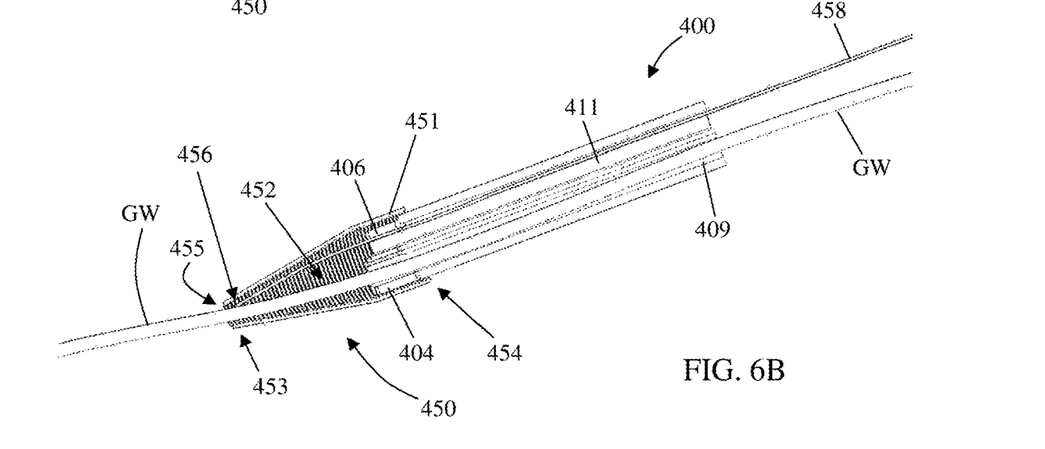
Figure 6C:
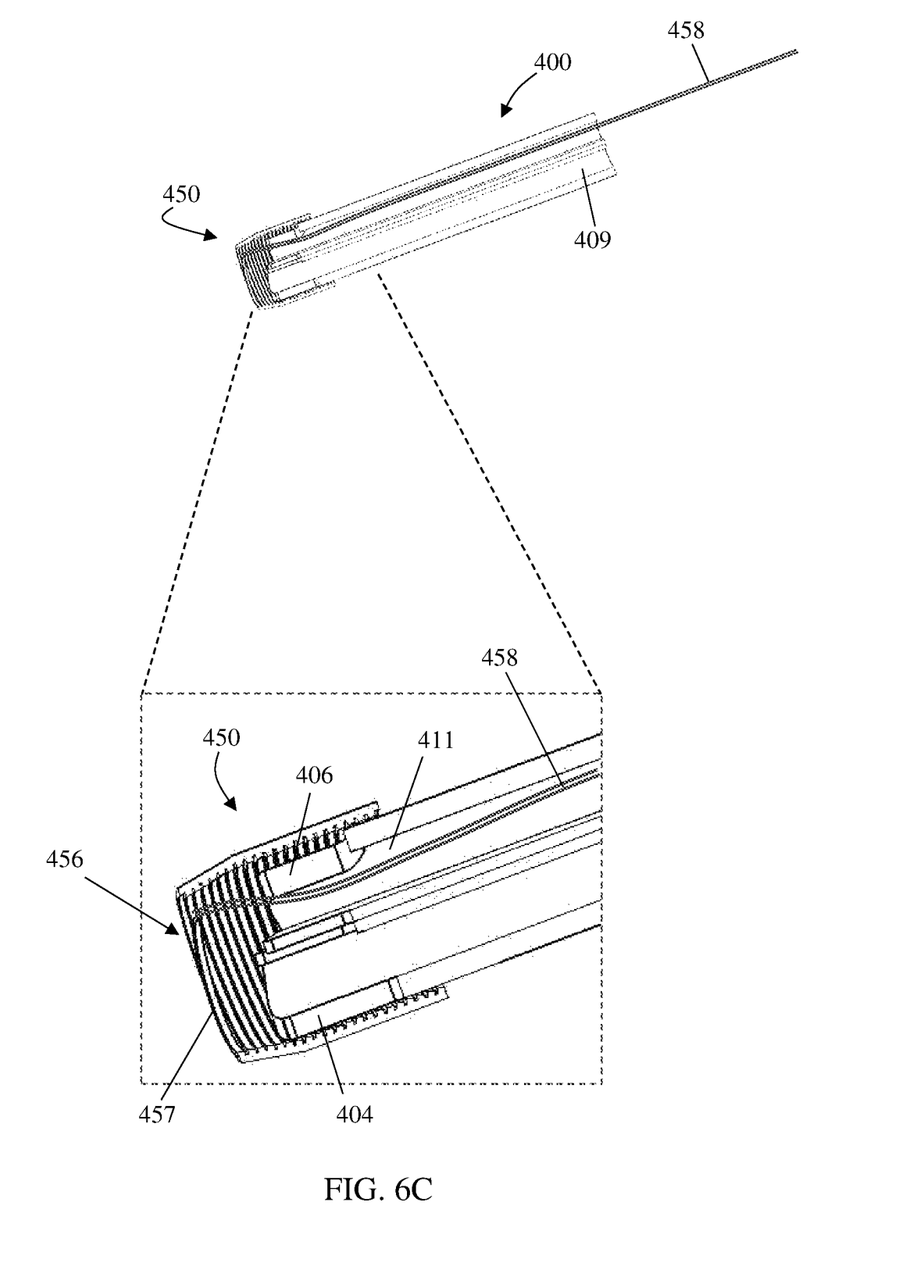

FIGS. 6A-6C are isometric views representing possible scenarios of implementing exemplary embodiments of a method for deploying catheter 400 of FIG. 5 with an exemplary atraumatic removable catheter cap 450. Atraumatic removable catheter cap 450 includes a thin-walled cap body 451 which encloses a cap cavity 452 between a cap vertex 453 and a cap base 454. Cap body 451 is sized and configured for housing distal end portion of catheter 400 with both first tip 404 and second tip 406, in cap cavity 452. Cap vertex 453 includes a guidewire opening 455 sized for passing a guidewire therethrough into first lumen 409 via cap cavity 452, for allowing progress of the catheter with the atraumatic removable catheter cap thereon in a blood vessel over a guidewire (e.g. by using an "over-the-wire" technique). Cap body 451 is configured for releasably adjoining distal end-portions of first tip 404 and second tip 406 the split-tip catheter, and the cap base 454 is sized to span at least around these distal end-portions when adjoined.

FIG. 6A shows catheter 400 after first tip 404 and second tip 406 are adjoined (e.g., manually) and immediately before capping distal end-portion of the catheter with atraumatic removable catheter cap 450. FIG. 6B shows catheter 400 fully capped with atraumatic removable catheter cap 450 and after passing a guidewire GW through guidewire opening 455 into first lumen 409 of the catheter 400, via cap cavity 452.

Atraumatic removable catheter cap 450 further includes a cap releasing member 456 which is sized and configured for passing along or/and through the catheter 400 and for operating release of cap body 451 from catheter 400 via proximal end of the catheter. In some embodiments, cap body 451 is transformable (e.g., dismantlable into one or more pieces) and configured for selective separation into at least one predefined constituent part that is sized, shaped or/and configured to freely pass through first lumen 409 or second lumen 411, by activation of cap release member 456. Optionally, cap body 451 includes splittable or/and peelable lines or portions, or/and it may be fabricated from at least one bonded or/and woven elongated member 457, optionally a single thread or a few threads, optionally made from soft wires but which are highly resistant to tears. A maximal sized piece of these one or more pieces may be sized or/and compressible to a compressed size for allowing passage via a lumen of the catheter, such as second lumen 411. In some embodiments, the cap releasing member 456 includes an elongated pulling member that is optionally in a form of a pull-wire 458. Dismantling of the atraumatic removable catheter cap 450 may include activating cap releasing member 456 via proximal end of the catheter, optionally by pulling pull-wire 458 (in a proximal direction). FIG. 6C shows catheter 400 during dismantling of cap body 456, in which the cap body is in reduced size.

The structure of atraumatic removable catheter cap 450 is optionally tapered relative to the guidewire GW, in order to allow smooth transition between the wire and cap. The atraumatic removable catheter cap 450 is optionally structurally robust for not collapsing upon insertion against resistance, especially at the skin. Optionally and additionally, atraumatic removable catheter cap 450 is impermeable to fluids such as blood, air or gas, for example if it is configured for insertion, while covering a catheter, into the abdominal cavity during laparoscopic procedures in which the cavity is inflated with gas, specifically $CO_2$. The peeling atraumatic removable catheter cap 450 over the catheter should be done by the operator, optionally after catheter 400 is in place. In some embodiments, means are provided to prevent early or premature peeling of the cap. The operator should be able to peel the cap with a single hand motion. The can should not damage the catheter tip when peeled.

Reference is made to FIGS. 7A-7E which are schematic sectional orthogonal views representing possible scenarios of implementing exemplary embodiments of a method for deploying a medical tube 500 (e.g., a catheter) in a body lumen BL (e.g., a blood vessel) with an exemplary atraumatic removable catheter cap 501, also using a reinforcing member 502. Atraumatic removable catheter cap 501 includes a cap body 503 enclosing a cap cavity 504 between a cap vertex 505 and a cap base 506. Atraumatic removable catheter cap 501 also includes a cap releasing mechanism 507 having an elongated pulling member in a form of a pull-wire 508, having a free proximal end 509. By pulling pull-wire 508 over a threshold force, against reinforcing member 502, cap body 503 is dismantlable into one or more pieces, which are removal through medical tube 500 (via one or more lumens thereof).

Reinforcing member 502 is sized and configured to resist shapeability of medical tube 500 or/and to fortify the medical tube from damage during dismantling atraumatic removable catheter cap 501 or/and pulling pull-wire 508. Such resisting is applicable to external forces including at least one of shearing forces, bending forces, twisting forces, axially compressing forces, flattening forces and kinking forces.

Figure 7A:
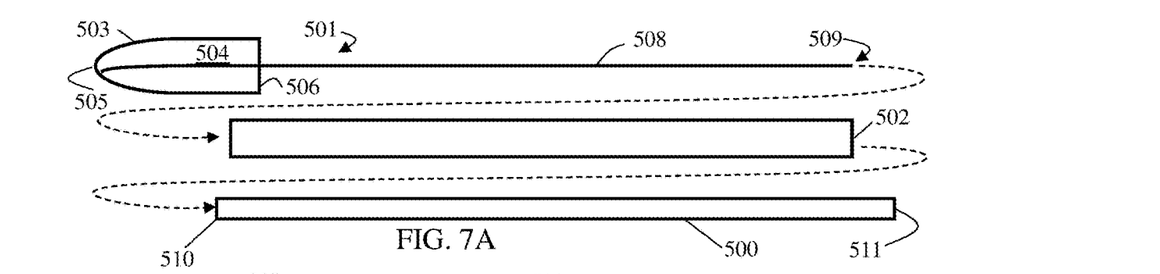
FIGS. 7A-7E are schematic sectional orthogonal views representing possible scenarios of implementing exemplary embodiments of a method for deploying a medical tube in a body lumen using a reinforcing member, in accordance with some embodiments of the invention.

FIG. 7A shows assembly of medical tube 500, atraumatic removable catheter cap 501, and reinforcing member 502, including the following steps (not necessarily in same order):

extending reinforcing member 502 along at least part of length of the medical tube 500, and capping a distal end-portion 510 of the medical tube 500 with the atraumatic removable catheter cap 501 and passing proximal end 509 of pull-wire 508 along and through the medical tube until pull-wire proximal end 509 protrudes out a proximal end 511 of the medical tube 500.

Figure 7B:
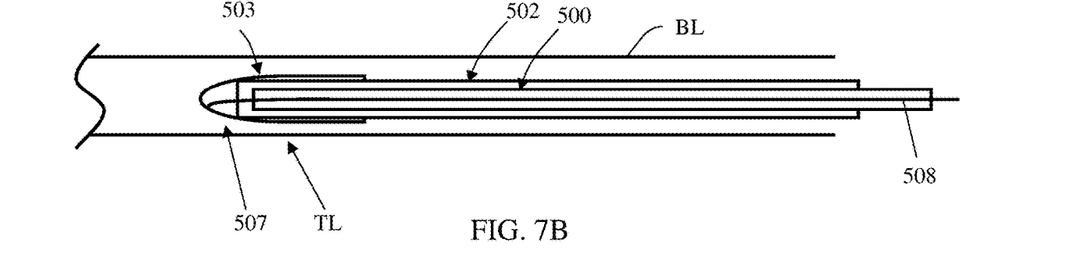

FIG. 7B shows pushing the assembly of medical tube 500, atraumatic removable catheter cap 501 thereon and reinforcing member 502, in the bodily lumen BL until reaching a target location TL.

Figure 7C:
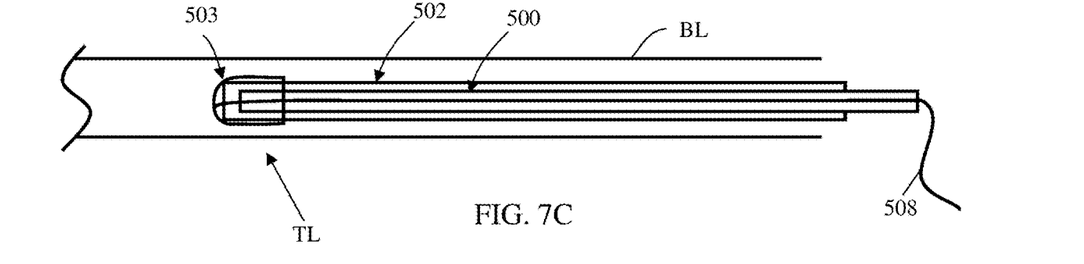
Figure 7D:
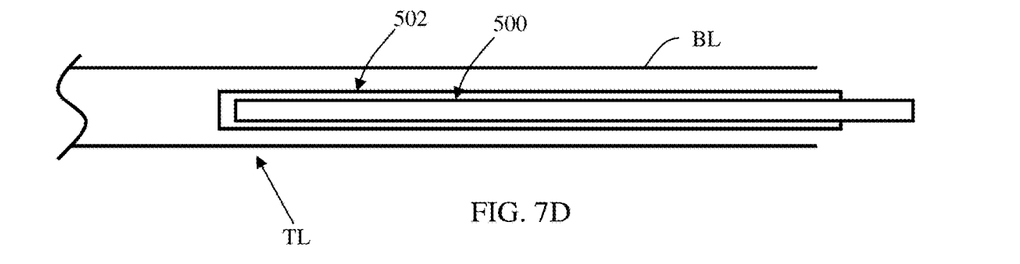

FIG. 7C shows medical tube 500 during dismantling of cap body 503, in which the cap body is of a reduced size. FIG. 7D shows medical tube 500 after complete dismantling of cap body 503 and removal thereof from medical tube 500 and bodily lumen BL.

Figure 7E:
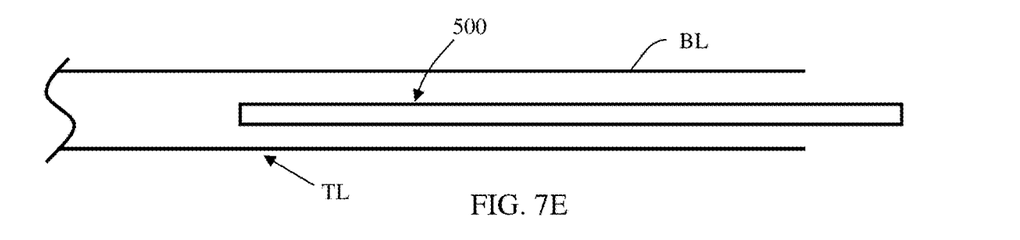

FIG. 7E shows medical tube 500 only in bodily lumen BL after removing reinforcing member 502 from bodily lumen BL.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. A removable catheter cap, comprising:
   a cap body configured for being removably connectable to a distal tip of a catheter, so as to facilitate capping of the distal tip of the catheter, wherein the cap body:
   is sized and shaped for blocking passage of the cap body through a lumen of the catheter extending from the catheter distal tip of the catheter to a proximal end of the catheter, and
   is transformable into at least one predefined constituent part that is sized and shaped to freely pass through the lumen of the catheter, the cap body including interbonded, intertwined, or/and woven separable windings, the separable windings configured to separate into the at least one predefined constituent part when the cap body is pulled against the distal tip of the catheter; and
   a cap releasing member configured to extend through the proximal end of the catheter when the removable catheter cap is connected to the catheter, the cap releasing member including a distal end directly connected to the at least one predefined constituent part, the cap releasing member being selectively manipulatable for disassembling the cap body into the at least one constituent part for facilitating withdrawal of the at least one constituent part from the distal tip of the catheter through the lumen of the catheter.

2. The removable catheter cap according to claim 1, wherein the cap releasing member is integral with an end portion of the at least one predefined constituent part that emerges from the cap body, and is extendable across the catheter lumen when the removable catheter cap is connected to the catheter.

3. The removable catheter cap according to claim 1, wherein the cap releasing member is selectively manipulatable for facilitating disconnection and release of the cap body from connection to the distal tip of the catheter.

4. The removable catheter cap according to claim 1, wherein the cap body includes a guidewire opening sized for passing a guidewire therethrough, so as to facilitate passage of the catheter, when connected to the removable catheter cap, over the guidewire in a blood vessel.

5. The removable catheter cap according to claim 1, wherein the cap body comprises a cap vertex and a cap base, wherein the cap body is configured with a cap cavity that spans between the cap vertex and the cap base, and the cap body is configured for housing the distal tip of the catheter.

6. The removable catheter cap according to claim 1, wherein the cap body includes splittable or/and peelable lines or portions that are configured to facilitate the disassembling of the cap body into the at least one predefined constituent part by separating the cap body along the splittable or/and peelable lines or portions.

7. The removable catheter cap according to claim 1, wherein the separable windings are configured to separate when the cap body is pulled against the distal tip of the catheter only above a predetermined pulling force.

8. The removable catheter cap according to claim 1, wherein the at least one predefined constituent part has an unwound free end configured as, or operatively connected to, an elongated pulling member, and the elongated pulling member is configured for transferring a pulling force to the cap body.

9. The removable catheter cap according to claim 8, wherein the cap releasing member includes, extends from, or is connected to, the elongated pulling member.

10. The removable catheter cap according to claim 1, wherein the cap body includes, or is releasably connected to, a first extension sized and configured for insertion into the catheter lumen.

11. The removable catheter cap according to claim 10, wherein the first extension, when extending into the catheter lumen, is configured to reinforce a distal portion of the catheter.

12. The removable catheter cap according to claim 1, wherein the catheter is a split-tip catheter comprising at least a first tip and a second tip, wherein the cap body is configured for releasably adjoining distal end-portions of the at least first tip and the second tip.

13. A removable catheter cap, comprising:
a cap body configured for being removably connectable to a distal tip of a catheter, so as to facilitate capping of the catheter distal tip, and is sized and shaped for blocking passage of the cap body through a lumen of the catheter extending from the catheter distal tip to a proximal end of the catheter, and the cap body includes interbonded, intertwined, or/and woven separable windings of at least one predefined constituent part that is sized and shaped to freely pass through the catheter lumen;
wherein the separable windings are configured to separate into the at least one predefined constituent part when the cap body is pulled against the catheter distal tip.

14. The removable catheter cap according to claim 13, wherein the at least one predefined constituent part has an unwound free end portion configured as, or operatively connected to, an elongated pulling member, and the elongated pulling member is configured for transferring a pulling force to the cap body.

15. The removable catheter cap according to claim 14, further comprising a cap releasing member that is configured to extend through the proximal end of the catheter, when the removable catheter cap is connected to the catheter, and is selectively manipulatable for facilitating transformation of the cap body into the at least one constituent part or/and for facilitating withdrawal of the at least one constituent part from the catheter distal tip through the catheter lumen.

16. A method for delivering a catheter in a blood vessel, the method comprising:
inserting a guidewire in the blood vessel and across a target location;
capping a distal tip of the catheter with a removable catheter cap comprising a cap body having a guidewire opening sized for passing the guidewire therethrough;
passing the guidewire through the guidewire opening, into and across a lumen of the catheter, to a proximal end of the catheter;
pushing the catheter with the removable catheter cap thereon in the blood vessel and over the guidewire until reaching the target location; and
disassembling the cap body into at least one predefined constituent part that is sized and shaped to pass freely through the catheter lumen, wherein disassembling comprises separating interbonded, intertwined, or/and woven windings of the cap body into the at least one predefined constituent part.

17. The method of claim 16, wherein the removable catheter cap includes a cap releasing member, and wherein the disassembling includes applying a pulling force to the cap releasing member from the proximal end of the catheter.

18. The method of claim 17, wherein the cap releasing member is, or is operatively connected to, an elongated pulling member extendable from the removable catheter cap through the distal tip of the catheter and to the proximal end of the catheter, wherein the disassembling includes pulling the elongated pulling member.

19. The method of claim 16, further comprising removing the at least one constituent part from the blood vessel via the catheter lumen.

* * * * *